United States Patent [19]

Majima et al.

[11] Patent Number: 5,036,004
[45] Date of Patent: Jul. 30, 1991

[54] PROCESS FOR PRODUCING L-SERINE

[75] Inventors: Eiji Majima; Hiroaki Takino, both of Kawasaki; Kunisuke Izawa, Yokohama; Kenzo Yokozeki; Koji Kubota, both of Kawasaki, all of Japan

[73] Assignee: Ajinomoto Co., Inc., Tokyo, Japan

[21] Appl. No.: 348,112

[22] Filed: May 5, 1989

Related U.S. Application Data

[63] Continuation of Ser. No. 813,557, Dec. 26, 1985, abandoned.

[30] Foreign Application Priority Data

Dec. 27, 1984 [JP] Japan ................. 59-281339
May 8, 1985 [JP] Japan ................. 60-96895
May 8, 1985 [JP] Japan ................. 60-96896
Jul. 17, 1985 [JP] Japan ................. 60-157153

[51] Int. Cl.$^5$ .................. C82P 13/06; C17N 1/12; C17N 1/14
[52] U.S. Cl. .................. 435/116; 435/252.1; 435/254
[58] Field of Search ............. 435/116, 829, 830, 836, 435/843, 849, 874, 252.1

[56] References Cited

FOREIGN PATENT DOCUMENTS 1139397 6/1986 Japan .................. 435/116

OTHER PUBLICATIONS

Yokozeki et al., *Agric. Biol. Chem.*, 51 (3), 963–964, 1987.
Sano et al., *Agric. Biol. Chem.*, 43 (1), pp. 2373–2374, 1979.
Kaneko et al., *Bull. Chem. Soc. Jap.*, 41, pp. 974–979, 1968.
Chemical Abstracts, vol. 103, No. 5, 5th Aug. 1985, p. 539, Abstract No. 37736r, Columbus, Ohio, U.S.; JP-A-60-34 937 (Showa Denko K.K.), 22-02-1985.
Patent Abstracts of Japan, vol. 1, No. 26, 26th Mar. 1977, p. 1084 C 76; & JP-A-51 136 619 (Ajinomoto K.K.), 26-11-1976 *Whole Abstract*.
Patent Abstracts of Japan, vol. 1, No. 111, 26th Sep. 1977, p. 2575 C 77; & JP-A-52 72 883 (Ajinomoto K.K.), 17-06-1977 *Whole Abstract.
Chemical Abstracts, vol. 105, No. 25, Dec. 1986, p. 624, Abstract No. 224600v, Columbus, Ohio, U.S.; & JP-A-61 139 397 (Showa Denko K.K.), 26-06-1986 *Whole Abstract*.

*Primary Examiner*—Douglas W. Robinson
*Assistant Examiner*—Irene Marx
*Attorney, Agent, or Firm*—Oblon, Spivak, McClelland, Maier & Neustadt

[57] ABSTRACT

A process for producing L-serine by the combination of chemical synthesis and enzyme chemical synthesis is disclosed. In this process L-serine is biochemically produced from 2-oxo-axazolidine-4-carboxylic acid or a salt thereof.

7 Claims, No Drawings

PROCESS FOR PRODUCING L-SERINE

This application is a Continuation of application Ser. No. 813,557, filed on Dec. 26, 1985, now abandoned.

BACKGROUND OF THE INVENTION

1. Field of the Invention:

The present invention relates to a process for biochemically producing L-serine from 2-oxo-oxazolidine-4-carboxylic acid or a salt thereof (hereinafter abbreviated as OOC) in a high yield.

2. Discussion of the Background:

L-Serine is an amino acid found in proteins. It is important as a medical or foodstuff additive or as a raw material for cosmetics.

L-Serine is widely found in nature as a component for constructing proteins. L-serine has been heretofore produced by hydrolyzing silk yarn, flocks, sericin, human hair, swine hair, etc., which all contain relatively large amounts of L-serine. The liberated L-serine is separated from other amino acids and purified. However, the yield is low in this process. And the process is not necessarily advantageous or economical because of restrictions in the supply of raw materials, etc.

Some processes for the chemical synthesis of L-serine are also known. However, their product is the optically inactive DL form of serine. Separating L-serine from a DL mixture involves complicated optical resolution, etc. which cannot be said to be an industrially feasible process for the production of L-serine.

As a process for producing L-serine by fermentation, there is known a process for producing it from glycine by using microorganisms of the genus Pseudomonas, etc. However, this process is not advantageous from point of view of yield, economical considerations, etc.

On the other hand, as a process for producing L-serine utilizing enzymes, there exists a process which utilizes serine hydroxymethyl transferase derived from animals and microorganisms. However, this process suffers the disadvantage that expensive tetrahydrofolate must be incorporated, in addition to glycine and formaldehyde. Furthermore, the process is disadvantageous in that the yield is poor.

Thus there is a strongly felt need for a process which readily provides optically pure L-serine in high yields and in an economically advantageous manner.

SUMMARY OF THE INVENTION

Accordingly, it is an object of this invention to provide a process for the ready production of L-serine.

It is another object of this invention to provide a process for the economical production of L-serine.

It is another object of this invention to provide a process for the facile production of L-serine in high yields.

Accordingly, the present invention provides a novel and efficient process for producing L-serine by the combination of chemical synthesis and enzyme chemical synthesis. This process satisfies all of the above objects of the invention. The present inventors have now surprisingly discovered that L-serine is readily produced by a process in which a cell treated product of a microorganism capable of producing L-serine from 2-oxo-oxazolidine-4-carboxylic acid or a salt thereof is reacted with 2-oxo-oxazolidine-4-carboxylic acid or salt thereof to produce L-serine.

DETAILED DESCRIPTION OF THE PREFERRED EMBODIMENTS

The present inventors have investigated various processes for producing L-serine by the combination of chemical synthesis and enzyme chemical synthesis and have thus discovered the present novel process for producing L-serine.

The present invention is directed to a process for producing L-serine by chemical synthesis in a simple and inexpensive manner. This process comprises reacting a cell treated product of microorganisms capable of producing L-serine from OOC or a salt thereof, with OOC or a salt thereof to produce L-serine. This invention also relates to a process for producing L-serine by reacting a microorganism capable of racemizing OOC or a salt thereof and a cell treated product of a microorganism capable of producing L-serine from OOC or a salt thereof, with OOC or a salt thereof to produce L-serine. The L-serine is then readily isolated.

Examples of the microorganisms capable of racemizing OOC or a salt thereof, and which can be used in the present invention include:

| | |
|---|---|
| Agrobacterium radiobacter | AJ 2782 |
| | ATCC 6466 |
| Alcaligenes marchallii | AJ 2147 |
| | ATCC 21030 |
| Arthrobacter citreus | AJ 1423 |
| | ATCC 11624 |
| Bacillus licheniformis | AJ 3290 |
| | ATCC 21417 |
| Beijerinchkia indica | AJ 2821 |
| | ATCC 9037 |
| Brevibacterium ammoniagenes | AJ 1443 |
| | ATCC 6871 |
| Corynebacterium acetoacidphilum | AJ 1550 |
| | ATCC 13870 |
| Escherichia coli | AJ 2621 |
| | ATCC 13070 |
| Mycobacterium ammoniaphilum | AJ 1997 |
| | ATCC 15354 |
| Micrococcus flavus | AJ 1021 |
| | ATCC 400 |
| Pseudomonas oleovorans | AJ 2058 |
| | ATCC 8062 |
| Saricina lutea | AJ 1217 |
| | ATCC 272 |
| Serratia marcescens | AJ 2686 |
| | ATCC 14225 | and the like.

Other bacteria than those described above may be used in the present invention, as long as they are microorganisms capable of racemizing OOC.

Next, examples of the microorganisms capable of producing L-serine by hydrolysis of OOC or a salt thereof, and which can be used in the present invention include:

| | |
|---|---|
| Alcaligenes faecalis | AJ 2541 |
| | FERM-P 8030, |
| | FERM-BP 940 |
| Arthrobacter grobiformis | AJ 1422 |
| | ATCC 8010 |
| Bacillus subtilis | AJ 1992 |
| | ATCC 13952 |
| Cellulomonas flavigena | AJ 1568 |
| | ATCC 491 |
| Corynebacterium hydrocarboclastus | FERM-P 1097 |
| Flavobacterium aquatile | AJ 2135 |
| | ATCC 8375 |
| Jensenia canicruria | AJ 3147 |

| | |
|---|---|
| | ATCC 11048 |
| *Mycobacterium ammoniaphilum* | AJ 1997 |
| | ATCC 15354 |
| *Micrococcus roseus* | AJ 1006 |
| | ATCC 9815 |
| *Rhodococcus erythropolis* | AJ 9126 |
| | ATCC 4277 |
| *Pseudomonas testosteroni* | AJ 2270 |
| | ATCC 17409 |
| *Pseudomonas acidovorans* | AJ 3117 |
| | ATCC 15668 |
| *Candida zeylanoides* | AJ 4677 |
| | IFO 0719 |
| *Citeromyces matritensis* | AJ 4287 |
| | CBS 2764 |
| *Cryptococcus laurentii* | AJ 5225 |
| | IFO 0609 |
| *Debaryomyces hansenii* | AJ 4179 |
| | IFO 0023 |
| *Endomycopsis oventensis* | AJ 5062 |
| | CBS 2508 |
| *Geotricum fragrans* | AJ 14298 |
| | CBS 15225 |
| *Hansenula californica* | AJ 5573 |
| | IFO 0800 |
| *Kluyveromyces marxianus* | AJ 4074 |
| | IFO 0219 |
| *Nadosonia falvescens* | AJ 5332 |
| | IFO 0666 |
| *Rhodotorula marina* | AJ 5014 |
| | IFO 0879 |
| *Torulopsis famata* | AJ 4342 |
| | IFO 0623 |
| *Trichosporon fermentans* | AJ 5152 |
| | IFO 1199 |
| *Wickerhamia fluorescens* | AJ 4285 |
| | IFO 1116 |
| *Achromobacter viscosus* | ATCC 12448 |
| *Aeromonas salmonicida* | ATCC 14174 |
| *Agrobacterium radiobacter* | ATCC 6466 |
| *Azotobacter vinelandii* | ATCC 9046 |
| *Brevibacterium pusillum* | ATCC 19096 |
| *Escherichia coli* | ATCC 13071 |
| *Klebsiella penumonia* | ATCC 8329 |
| *Kluyvera non-citrophila* | FERM-P 3150 |
| *Kurthina zophii* | ATCC 6900 |
| *Mycoplana dimorpha* | ATCC 4279 |
| *Proteus rettgeri* | FERM-P 8196, FERM-BP 941 |
| | AJ 2770 |
| *Salmonella schottmuelleri* | ATCC 8759 |
| *Serratia marcescens* | ATCC 14225 |
| *Streptomyces humifer* | FERM-P 2347 |
| *Vibrio-tyrogenes* | ATCC 7085 |
| *Xantomonas canpestris* | ATCC 7381 |
| *Pichia membranaefaciens* | IFO 0460 |
| *Saccharomyces fermentati* | IFO 0422 |
| *Tremella brasiliensis* | IFO 9289 |
| *Alternaria cucumerina* | IFO 7417 |
| *Curvularia geniculata* | ATCC 6671 |
| *Fusarium nivale* | ATCC 42308 |
| *Helminthosporium gramineum* | ATCC 6695 |
| *Phoma destructiva* | ATCC 24636 |
| *Sclerotium bataticola* | ATCC 12265 |
| *Cochliobolus miyabeanus* | IFO 5844 |
| *Mucor circinelloides* | ATCC 8770 |
| *Aspergillus repens* | ATCC 5817 |
| *Penicillium decumbens* | ATCC 10436 |
| *Gromerella cingulata* | ATCC 11326 |
| *Septoria glycines* | ATCC 38699 |
| *Pseudoplea trifolii* | IFO 7252 |
| *Stemphylium astragali* | IFO 7244 |
| *Diplodia natalensis* | ATCC 34643 |
| *Stachylidium bicolor* | ATCC 12672 |
| *Eupenicillium alutaceum* | ATCC 18542 |
| *Anixiella reticulata* | ATCC 34511 |
| *Arachniotus flavoluteus* | ATCC 18430 |
| *Byssochlamys fulva* | ATCC 10099 |
| *Coniochaeta tetraspora* | ATCC 22275 |
| *Golasinospora longispora* | ATCC 18493 |
| *Gymnoascus umbrinus* | IFO 8358 |
| *Microascus cinereus* | ATCC 16594 |
| *Microthecium retisporum* | ATCC 22184 |
| *Sordaria humana* | ATCC 22796 |
| *Sporormiella isomera* | ATCC 24341 |
| *Toxotrichum cancellatum* | ATCC 15316 |
| *Melanospora zamiae* | ATCC 12340 | and the like.

*Alcaligenes faecalis* (FERM-P 8030) was originally deposited on Dec. 24, 1984, and *Proteus rettgeri* (FERM-P 8196) was originally deposited on Apr. 25, 1985 at the Fermentation Research Institute, Agency of Industrial Sciences and Technology, Ministry of International Trade and Industry (FRI), 1-3, Higashi 1-Chome, Yatabo-machi, Tsukuba-gun, Ibaragi-ken 305, Japan, and were accorded the FERM-P numbers indicated above. The microorganisms deposited were then converted into deposits under the Budapest Treaty on Nov. 24, 1985, and were accorded the corresponding FERM-BP numbers.

Microorganisms other than the bacteria described above may be used as the bacteria in the present invention, as long as they are microorganisms capable of producing L-serine through the decomposition of OOC.

Ordinary nutrient media may be appropriately used as the media for culturing the microorganisms capable of racemizing OOC and the microorganisms capable of producing L-serine by hydrolyzing OOC as described above. As carbon sources, there may be used, for example, sugars such as glucose, sucrose, glycerol, molasses, etc.; organic acids such as fumaric acid, acetic acid, etc.; alcohols such as ethanol, methanol, etc. As nitrogen sources, there may be used ammonium sulfate, ammonium chloride, etc. and as organic nutrient sources, there may be used yeast extract, peptone, meat extract, corn steep liquor, etc. As inorganic ions, there may be used ions of magnesium, iron, manganese, potassium, sodium, phosphoric acid, etc. and as vitamins, pyridoxine, pyridoxal phosphate, etc.

Incubation may be carried out in a conventional manner. For example, the pH of the medium is adjusted to 6 to 9 and the bacteria of the present invention are aerobically cultured at 20° to 40° C. for 1 to 3 days. Upon incubation, the culture or cell product having a high capability of hydrolysis or racemization may be obtained sometimes by incorporating a small quantity of OOC in the medium.

The cell treated product used in the present invention refers to a product which possesses activity of racemizing OOC. Examples of such cell treated products include a culture solution per se, a solution obtained by separating cells from the culture solution, separated cells, decomposition products of the separated cells, purified decomposition products, etc. These cell treated products may be used as they are, or may be subjected to treatments such as freeze drying, drying with acetone, etc. Alternatively, the products may be subjected to immobilization, etc.

The concentration of a substrate in enzyme reaction may vary depending upon batch system or continuous system, but generally it is from 0.1 to 30% in an aqueous medium, preferably 0.5 to 10%, in the batch system; in the continuous system, it is preferred that the concentration be somewhat lower than the above ranges.

The reaction is carried out generally in an aqueous medium, at 15° to 60° C., preferably at about 30° to about 40° C., at pH of 4 to 10, preferably about 7. The reaction time is not the same since it varies depending upon means of settling, stirring, flowing, etc. and mode or titer of enzyme standard. However, in the batch system, the reaction time is generally for about 10 minutes to about 72 hours.

In case that cells of the above-described microorganisms are brought into contact with OOC while culturing the cells in an aqueous medium, the aqueous medium containing OOC and further containing nutrient sources required for growth of the microorganisms such as carbon sources, nitrogen sources, inorganic ions, etc. are used. In addition, the incorporation of organic trace nutrients such as vitamins, amino acids, etc. often give desired results.

As carbon sources, carbohydrates such as glucose, sucrose, etc., organic acids such as acetic acid, etc., alcohols and the like may be appropriately used. As nitrogen sources, ammonia gas, ammonia water, ammonium salts and the like may be used. As inorganic ions, magnesium ions, phosphate ions, potassium ions, iron ions and the like may be appropriately used depending upon necessity.

The incubation is carried out while controlling the conditions within appropriate ranges at pH or 4 to 8 at temperatures of 25° to 40° C. under aerobic conditions, whereby desired results can be obtained.

On the other hand, in case that the culture solution of the above-described microorganisms are reacted with OOC as they are, or the cultured cells or cell treated products are reacted by bringing them into contact with OOC, OOC and the culture solution, or an aqueous medium in which the cultured cells or cell treated products are dissolved or suspended may be settled or stirred for a while while controlling the temperature to a suitable range between 15° to 60° C. and keeping the pH at 4 to 10. Thus after 10 minutes to 72 hours passes, large quantities of racemic compounds or hydrolytic products of OOC are produced and accumulated in the aqueous medium.

A quantitative analysis of the D-form and the L-form was run by liquid chromatography using a resin for optical resolution to determine whether or not the OOC was racemized by the enzyme reaction in the present invention. Further NMR spectrum, X-ray diffraction pattern, liquid chomatography, quantitative assay data for bioassay, specific rotary power data, etc. was obtained from the serine crystals obtained in the examples later described to determine whether or not L-serine was produced by the hydrolysis of OOC through the enzyme reaction.

Other features of the invention would become apparent in the course of the following descriptions of exemplary embodiments which are given for illustration of the invention and are not intended to be limiting thereof.

EXAMPLE 1

A 500 ml volume flask was charged with 50 ml of medium (pH 7.0) containing 2% of glycerol, 0.5% of yeast extract, 0.5% of peptone, 0.25% of NaCl, 0.2% of DL-OOC and 4.0% of calcium carbonate (separately sterilized) and sterilized at 120° C. for 15 minutes. A microorganism shown in Table 1 cultured at 30° C. for 24 hours in bouillon-agar medium was inoculated on the medium. After culturing at 30° C. for 24 hours, the cells were centrifuged, washed and collected. The cells were added to acetate buffer (0.1M at the end; terminal pH, 4.0) or phosphate buffer (0.1M at the end terminal pH, 7.0) or tris buffer (0.1M at the end; terminal pH, 8.5) containing 1% of D-OOC in a 5% concentration calculated as bacterial cells. The mixture was settled at 30° C. for 24 hours to react them. After completion of the reaction, L-OOC produced was quantitatively determined by liquid chromatography using a resin for optical resolution. The results are shown in Table 1.

TABLE 1

Amount of L-OOC Produced by Various Microorganisms at pH of 4.0, 7.0 or 8.5

| Microorganism | Amount of L-OOC Produced [mg/dl] | | |
|---|---|---|---|
| | pH 4.0 | pH 7.0 | pH 8.5 |
| *Agrobacterium radiobacter* ATCC 6466 | 0 | 45 | 171 |
| *Alcaligenes marchallii* ATCC 21030 | 18 | 128 | 264 |
| *Arthrobacter citreus* ATCC 11624 | 16 | 25 | 85 |
| *Bacillus licheniformis* ATCC 21417 | 43 | 479 | 362 |
| *Beijerinchkia indica* ATCC 9037 | 0 | 158 | 341 |
| *Brevibacterium ammoniagenes* ATCC 6871 | 25 | 417 | 477 |
| *Corynebacterium acetoacidphilum* ATCC 13870 | 29 | 262 | 265 |
| *Escherichia coli* ATCC 13070 | 41 | 68 | 0 |
| *Mycobacterium ammoniaphilum* ATCC 15354 | 0 | 174 | 314 |
| *Micrococcus flavus* ATCC 400 | 0 | 245 | 315 |
| *Pseudomonas oleovorans* ATCC 8062 | 18 | 164 | 207 |
| *Saricina lutea* ATCC 272 | 0 | 158 | 70 |
| *Serratia marcescens* ATCC 14225 | 76 | 29 | 0 |

EXAMPLE 2

In 50 ml of medium similar to Example 1 charged in a 500 ml flask, *Bacillus licheniformis* (ATCC 21417) was cultured at 30° C. for 16 hours. Into the culture solution was sterilizingly poured 10 ml of an aqueous solution (adjusted pH to 7.0) containing 500 mg of D-OOC. After adjusting the pH of the culture solution to 7.0 under sterilized conditions, incubation was carried out for an additional 10 hours. During the incubation, the pH was sterilizingly adjusted to 7.0 every two hours.

A part of the culture solution was withdrawn to quantitatively determine L-OOC by liquid chromatography using a resin for optical resolution. L-OOC was formed in an amount of 406 mg/dl.

EXAMPLE 3

*Bacillus licheniformis* (ATCC 21417) was inoculated on 50 ml of medium similar to Example 1 charged in a 500 ml flask. After culturing at 30° C. for 16 hours, the cells were centrifuged, washed and collected. The cells were added to phosphate buffer (0.1M at the end; terminal pH, 7.0) containing 1% of L- or D-OOC in a concentration of 5% calculated as bacteria followed by reaction by settling at 30° C. for 18 hours. After completion of the reaction, D-OOC or L-OOC in the reaction solution by liquid chromatography using a resin for optical resolution was quantitatively determined. The results are shown in Table 2.

TABLE 2

Amount of L- or D-OOC Produced When L- or D-OOC is Used as Substrate

| Amount of OCC Prior to Reaction [mg/dl] | | Amount of OOC Reaction [mg/dl] | |
| --- | --- | --- | --- |
| L-OOC | 1000 | L-OOC: | 509 |
| | | D-OOC: | 473 |
| D-OOC | 1000 | L-OOC: | 492 |
| | | D-OOC: | 471 |

EXAMPLE 4

In 50 ml of medium similar to Example 1 charged in a 500 ml flask, *Bacillus licheniformis* (ATCC 21417) was cultured at 30° C. for 16 hours. After adding 5 ml of a 4% sodium alginate solution to 5 ml of a suspension of the cells in physiological saline in a concentration of 20 g/dl to mix them, the mixture was slowly dropwise added to a 15 g/dl calcium chloride solution to prepare bead-like immobilized cells. The total amount of the immobilized cells were poured into phosphate buffer (0.1M at the end; terminal pH, 7.0) containing 1% D-OOC followed by reacting at 30° C. for 16 hours. As a result, D-OOC was racemized and 432 mg/dl of L-OOC was formed in the reaction solution.

EXAMPLE 5

In a 500 ml volume flask was charged 50 ml of medium (ph 7.0) containing 2% of glycerol, 0.5% of yeast extract, 0.5% of peptone, 0.25% of NaCl, 0.2% of DL-OOC and 4.0% of calcium carbonate (separately sterilized) followed by sterilization at 120° C. for 15 minutes.

A platinum earpick of microorganism shown in Table 3 cultured at 30° C. for 24 hours in bouillon-agar medium was inoculated on the medium. After culturing at 30° C. for 20 hours, the cells were collected from the culture solution by centrifugation. The cells were washed with an equivalent amount of physiological saline to that of the culture solution. The cells were collected and added to a reaction solution containing 1% of L-OOC, pH of which had been adjusted to 7 or 8.5 in a 5% concentration calculated as cells. The mixture was settled at 30° C. for 48 hours to react them. After completion of the reaction, L-serine was quantitatively determined by bioassay. The results are shown in Table 3.

TABLE 3

Amount of L-Serine Accumulated in Various Microorganisms at pH 7.0 or pH 8.5

| Microorganism | Amount of L-Serine Accumulated [mg/dl] | |
| --- | --- | --- |
| | pH 7.0 | pH 8.5 |
| *Alcaligenes faecalis* AJ 2541, FERM-BP 940 | 20 | 58 |
| *Arthrobacter grobiformis* ATCC 8010 | 4 | 10 |
| *Bacillus subtilis* ATCC 13952 | 10 | 13 |
| *Cellulomonas flavigena* ATCC 491 | 41 | 31 |
| *Corynebacterium hydrocarboclastus* FERM-P 1097 | 4 | 14 |
| *Flavobacterium aquatile* ATCC 8375 | 26 | 23 |
| *Jensenia canicruria* ATCC 11048 | 18 | 23 |
| *Mycobacterium ammoniaphilum* ATCC 15354 | 66 | 42 |
| *Micrococcus roseus* ATCC 9815 | 124 | 26 |
| *Rhodococcus erythropolis* ATCC 4277 | 26 | 23 |
| *Pseudomonas testosteroni* ATCC 17409 | 368 | 132 |
| *Pseudomonas acidoverans* ATCC 17409 | 328 | 142 |
| *Candida zeylanoides* IFO 0719 | 28 | 36 |
| *Citeromyces matritensis* CBS 2764 | 15 | 23 |
| *Cryptococcus laurenti* IFO 0609 | 15 | 39 |
| *Debaryomyces hansenii* IFO 0023 | 13 | 29 |
| *Endomycopsis oventensis* CBS 2508 | 30 | 33 |
| *Geotricum fragrans* CBS 15225 | 20 | 26 |
| *Hansenula californica* IFO 0800 | 17 | 26 |
| *Kluyveromyces marxianus* IFO 0219 | 20 | 33 |
| *Nadosonia falvescens* IFO 0666 | 15 | 19 |
| *Rhodotorula marina* IFO 0879 | 20 | 54 |
| *Torulopsis famata* IFO 0623 | 20 | 28 |
| *Trichosporon fermentans* IFO 1199 | 24 | 33 |
| *Wickerhamia fluorescens* IFO 1116 | 28 | 36 |
| *Achromobacter viscosus* ATCC 12448 | 95 | 121 |
| *Aeromonas salmonicida* ATCC 14174 | 58 | 0 |
| *Agrobacterium radiobacter* ATCC 6466 | 32 | 94 |
| *Azotobacter vinelandii* ATCC 9046 | 5 | 0 |
| *Brevibacterium pusillum* ATCC 19096 | 36 | 9 |
| *Escherichia coli* ATCC 13071 | 14 | 2 |
| *Klebsiella penumonise* ATCC 8329 | 12 | 26 |
| *Kluyvera non-citrophilia* FERM-P 3150 | 0 | 36 |
| *Kurthina sophii* ATCC 6900 | 22 | 7 |
| *Mycoplana dimorpha* ATCC 4279 | 35 | 30 |
| *Proteus-rettgeri* AJ 2770, FERM BP-941 | 31 | 4 |
| *Salmonella shottmuelleri* ATCC 8759 | 51 | 43 |
| *Serratia marcescens* ATCC 14225 | 57 | 25 |
| *Streptomyces humifer* FERM-P 2347 | 0 | 31 |
| *Vibrio tyrogenes* ATCC 7085 | 27 | 52 |
| *Xanthomonas campestris* ATCC 7381 | 17 | 20 |
| *Pichia membranaefaciens* IFO 0460 | 48 | 37 |
| *Saccharomyces fermentati* IFO 0422 | 63 | 42 |
| *Tremella brasiliensis* IFO 9289 | 47 | 33 |
| *Alternaria cucumerina* IFO 7417 | 98 | 12 |
| *Curvularia geniculata* ATCC 6671 | 195 | 79 |
| *Fusarium nivale* ATCC 42308 | 117 | 54 |

TABLE 3-continued

Amount of L-Serine Accumulated in Various Microorganisms at pH 7.0 or pH 8.5

| Microorganism | Amount of L-Serine Accumulated [mg/dl] | |
|---|---|---|
| | pH 7.0 | pH 8.5 |
| Helminthosporium gramineum ATCC 6695 | 183 | 71 |
| Phoma destructiva ATCC 24636 | 103 | 86 |
| Sclerotium bataticola ATCC 12265 | 155 | 140 |
| Cochliobolus miyabeanus IFO 5844 | 264 | 71 |
| Mucor circinelloides ATCC 8770 | 113 | 48 |
| Aspergillus repens ATCC 5817 | 192 | 76 |
| Penicillium decumbens ATCC 10436 | 102 | 24 |
| Gromerella cingulata ATCC 11326 | 31 | 0 |
| Septoria glycines ATCC 38699 | 51 | 3 |
| Pseudoplea trifolii IFO 7252 | 77 | 32 |
| Stemphylium astragali IFO 7244 | 8 | 0 |
| Diplodia natalensis ATCC 34643 | 42 | 0 |
| Stachylidium bicolor ATCC 12672 | 70 | 6 |
| Eupenicillium alutaceum ATCC 18542 | 35 | 7 |
| Anixiella reticulata ATCC 34511 | 102 | 35 |
| Arachniotus flavoluteus ATCC 18430 | 84 | 0 |
| Byssochlamys fulva ATCC 10099 | 51 | 16 |
| Coniochaeta tetraspora ATCC 22275 | 36 | 0 |
| Golasinospora longispora ATCC 18493 | 45 | 3 |
| Gymnoascus umbrinus IFO 8358 | 102 | 25 |
| Microascus cinereus ATCC 16594 | 50 | 8 |
| Microthecium retisporum ATCC 22184 | 100 | 23 |
| Sordaria humana ATCC 22796 | 171 | 43 |
| Sporormiella isomera ATCC 24341 | 152 | 14 |
| Toxotricum cancellatum ATCC 15316 | 35 | 0 |
| Melanospora zamiae ATCC 12340 | 81 | 10 |

EXAMPLE 6

In 50 ml of medium similar to Example 1 charged in a 500 ml flask, *Pseudomonas acidovorans* (ATCC 15668) was cultured at 30° C. for 12 hours. Into the culture solution was sterilizingly poured 10 ml of an aqueous solution (adjusted pH to 7.0) containing 500 mg of DL-OOC. After adjusting pH of the culture solution to 7.0 under sterilized conditions, incubation was carried out for further 10 hours. During the incubation, the pH was sterilizingly adjusted to 7.0 in every two hours.

A part of the culture solution was withdrawn and appropriately diluted to quantitatively determine L-serine by bioassay. L-OOC was formed in an amount of 288.3 mg/dl.

EXAMPLE 7

*Pseudomonas testosteroni* (ATCC 17409) was inoculated on 50 ml of medium similar to Example 5 charged in a 500 ml flask. After culturing at 30° C. for 16 hours, the culture solution was centrifuged, washed and freeze dried. The cells were suspended in 1 liter of an enzyme reaction solution in a 5% concentration. The enzyme reaction solution comprised 1% of L-OOC and 1% of $KH_2PO_4$. The reaction was performed by settling at pH of 7.0 at 30° C. for 48 hours. After completion of the reaction, the reaction mixture was centrifuged. The supernatant was taken. A part of the supernatant was appropriately diluted and L-serine produced was quantitatively assayed by bioassay.

L-Serine accumulated in an amount of 3.42 mg/dl (molar yield, 45%).

On the other hand, after completion of the reaction, the reaction mixture was centrifuged to remove the bacteria. After the supernatant was obtained, 5 g of activated charcoal was added. The mixture was heated and filtered to obtain 990 ml of the supernatant. After the supernatant was concentrated under reduced pressure, the pH was adjusted to 3.0 and passed through a column packed with 500 ml of cationic ion exchange resin Dia Ion SK-1B. After washing with 2000 ml of distilled water, elution was performed with 2N ammonia water to collect serine fractions. After pH of the concentrate was adjusted to 5.7, approximately 2-fold amount of methanol was slowly added thereto at low temperature to precipitate L-serine crystals. The system was allowed to stand for further a day at 10° C. The precipitated crystals were separated by filtration, washed with methanol and dried to obtain 1.2 g of the crystals.

EXAMPLE 8

In 50 ml of medium similar to Example 1 charged in a 500 ml flask, *Pseudomonas testosteroni* (ATCC 17409) was cultured at 30° C. for 16 hours. The cells were suspended in physiological saline in a concentration of 20 g/dl and 5 ml of a 4% sodium alginate solution was added to 5 ml of the suspension. After mixing them, the mixture was slowly dropwise added to a 15 g/dl calcium chloride solution to prepare bead-like immobilized cells. The whole amount of the immobilized cells was poured into phosphate buffer (0.1M at the end) terminal pH, 7.0) containing 1% of L-OOC followed by reacting at 30° C. for 16 hours. As a result, 354 mg/dl of L-serine was formed.

EXAMPLE 9

*Bacillus licheniformis* (ATCC 21417) was inoculated on medium similar to Example 1. After culturing at 30° C. for 16 hours, the cells were centrifuged, washed and collected. The cells were added to phosphate buffer (0.1M at the end; terminal pH, 7.0) containing 1% of D-OOC in a 5% concentration calculated as cells. The system was settled at 30° C. for 48 hours to react them. After completion of the reaction, a 5% concentration as cells of *Pseudomonas testosteroni* (ATCC 17409) cultured under the same conditions was added to the reaction solution. The mixture was settled at 30° C. for further 48 hours to react them. After completion of the reaction, L-serine was quantitatively determined by bioassay, whereby 359 mg/dl of L-serine was formed. On the other hand, when only viral cells of *Pseudomonas testosteroni* (ATCC 17409) was reacted, no formation of L-serine was observed.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A process for producing L-serine, comprising:
reacting a microorganism capable of producing L-serine from L-2-oxo-oxazolidine-4-carboxylic acid or a salt thereof, with L-2-oxo-oxazolidine-4-carboxylic acid or salt thereof in a culture medium to produce L-serine, wherein said microorganism is selected from the group consisting of *Alcaligenes faecalis* AJ 2541, FERM-P 8030, FERM-BP 940, *Arthrobacter globiformis* AJ 1422, ATCC 8010, *Bacillus subtilis*, AJ 1992, ATCC 13952, *Cellulomonas flavigena* AJ 1568, ATCC 491, *Corynebacterium hydrocarboclastus* FERM-P 1097, *Flavobacterium aquatile* AJ 2135, ATCC 8375, *Jensenia canicruria* AJ 3147, ATCC 11048, *Mycobacterium ammoniaphilum* AJ 1977, ATCC 15354, *Micrococcus roseus* AJ 1006, ATCC 9815, *Rhodococcus erythropolis* AJ 9126, ATCC 4277, *Pseudomonas testosteroni* AJ 2270, ATCC 17409, *Pseudomonas acidovorans* AJ 3117, ATCC 15668, *Candida zeylanoides* AJ 4677, IFO 0719, *Citeromyces matritensis* AJ 4287, CBS 2764, *Cryptococcus laurentii* AJ 5225, IFO 0609, *Debaryomyces hansenii* AJ 4179, IFO 0023, *Endomycopsis oventensis* AJ 5062, CBS 2508, *Geotricum fragrans* AJ 14298, CBS 15225, *Hansenula californica* AJ 5573, IFO 0800, *Kluyveromyces marxianus* AJ 4074, IFO 0219, *Nadosonia falvescens* AJ 5332, IFO 0666, *Rhodotorula marina* AJ 5014, IFO 0879, *Torulopsis famata* AJ 4342, IFO 0623, *Trichosporon fermentans* AJ 5152, IFO 1199, *Wickerhamia fluorescens* AJ 4285, IFO 1116, *Achromobacter viscosus* ATCC 12448, *Aeromonas salmonicida* ATCC 14174, *Agrobacterium radiobacter* ATCC 6466, *Azotobacter vinelandii* ATCC 9046, *Brevibacterium pusillum* ATCC 19096, *Escherichia coli* ATCC 13071, *Klebsiella pneumonia* ATCC 8329, *Kluyvera non-citrophila* FERM-P 3150, *Kurthina zophii* ATCC 6900, *Mycoplana dimorpha* ATCC 4279, *Proteus rettgeri* FERM-P 8196, FERM-BP 941, AJ 2770, *Salmonella schottmuelleri* ATCC 8759, *Serratia marcescens* ATCC 14225, *Streptomyces humifer* FERM-P 2347, *Vibrio-tyrogenes* ATCC 7085, *Xanthomonas campestris* ATCC 7381, *Pichia membranaefaciens* IFO 0406, *Saccharomyces fermentati* IFO 0422, *Tremella brasiliensis* IFO 9289, *Alternaria cucumerina* IFO 7417, *Curvularia geniculata* ATCC 6671, *Fusarium nivale* ATCC 42308, *Helminthosporium gramineum* ATCC 6695, *Phoma destructiva* ATCC 24636, *Sclerotium bataticola* ATCC 12265, *Cochliobolus miyabeanus* IFO 5844, *Mucor circinelloides* ATCC 8770, *Aspergillus repens* ATCC 5817, *Penicillium decumbens* ATCC 10436, *Gromerella cingulata* ATCC 11326, *Septoria glycines* ATCC 38699, *Pseudoplea trifolii* IFO 7252, *Stemphylium astragali* IFO 7244, *Diplodia natalensis* ATCC 34643, *Stachylidium bicolor* ATCC 12672, *Eupenicillium alutaceum* ATCC 18542, *Anixiella reticulata* ATCC 34511, *Arachniotus flavoluteus* ATCC 18430, *Byssochlamys fulva* ATCC 10099, *Coniochaeta tetraspora* ATCC 22275, *Golasinospora longispora* ATCC 18493, *Gymnoascus umbrinus* IFO 8358, *Microascus cinereus* ATCC 16594, *Microthecium retisporum* ATCC 22184, *Sordaria humana* ATCC 22796, *Sporormiella isomera* ATCC 24341, *Toxotrichum cancellatum* ATCC 15316 and *Melanospora zamiae* ATCC 12340; and obtaining L-serine from said medium.

2. A process for producing L-serine, comprising:
reacting a first microorganism capable of racemizing D-2-oxo-oxazolidine-4-carboxylic acid with D-oxo-oxazolidine-4-carboxylic acid or a salt thereof, to obtain D,L-2-oxo-oxazolidine-4-caroxylic acid or a salt thereof, wherein said first microorganism is selected from the group consisting of *Agrobacterium radiobacter* AJ 2782, ATCC 6466, *Alcaligenes marchallii* AJ 2167, ATCC 21030, *Arthrobacter citreus* AJ 1423, ATCC 11624, *Bacillus licheniformis* AJ 3290, ATCC 21417, *Beijerinchkia indica* AJ 2821, ATCC 9037, *Brevibacterium ammoniagenes* AJ 1443, ATCC 6871, *Corynebacterium acetoacidophilum* AJ 1550, ATCC 13870, *Escherichia coli* AJ 2621, ATCC 13070, *Mycobactrium ammoniaphilum* AJ 1997, ATCC 15354, *Micrococcus flavus* AJ 1021, ATCC 400, *Pseudomonas oleovorans* AJ 2058, ATCC 8062, *Saricina lutea* AJ 1217, ATCC 272, and *Serratia marcescens* AJ 2686, ATCC 14225; and reacting a second microorganism capable of producing L-serine from L-2-oxo-oxazolidine-4-carboxylic acid or a salt thereof, with L-2-oxo-oxazolidine-4-carboxylic acid or a salt thereof in a culture medium to produce L-serine, wherein said second microorganism is selected from the group consisting of *Alcaligenes faecalis* AJ 2541, FERM-P 8030, FERM-BP 940, *Arthrobacter globiformis* AJ 1422, ATCC 8010, *Bacillus subtilis*, AJ 1992, ATCC 13952, *Cellulomonas flavigena* AJ 1568, ATCC 491, *Corynebacterium hydrocarboclastus* FERM-P 1097, *Flavobacterium aquatile* AJ 2135, ATCC 8375, *Jensenia canicruria* AJ 3147, ATCC 11048, *Mycobacterium ammoniaphilum* AJ 1997, ATCC 15354, *Micrococcus roseus* AJ 1006, ATCC 9815, *Rhodococcus erythropolis* AJ 9126, ATCC 4277, *Pseudomonas testosteroni* AJ 2270, ATCC 17409, *Pseudomonas acidovorans* AJ 3117, ATCC 15668, *Candida zeylanoides* AJ 4677, IFO 0719, *Citeromyces matritensis* AJ 4287, CBS 2764, *Cryptococcus laurentii* AJ 5225, IFO 0609, *Debaryomyces hansenii* AJ 4179, IFO 0023, *Endomycopsis oventensis* AJ 5062, CBS 2508, *Geotricum fragrans* AJ 14298, CBS 15225, *Hansenula californica* AJ 5573, IFO 0800, *Kluyveromyces marxianus* AJ 4074, IFO 0219, *Nadosonia falvescens* AJ 5332, IFO 0666, *Rhodotorula marine* AJ 5014, IFO 0879, *Torulopsis famata* AJ 4342, IFO 0623, *Trichosporon fermentans* AJ 5152, IFO 1199, *Wickerhamia fluorescens* AJ 4285, IFO 1116, *Achromobacter viscosus* ATCC 12448, *Aeromonas salmonicida* ATCC 14174, *Agrobacterium radiobacter* ATCC 6466, *Azotobacter vinelandii* ATCC 9046, *Brevibacterium pusillum* ATCC 19096, *Escherichia coli* ATCC 13071, *Klebsiella pneumonia* ATCC 8329, *Kluyvera non-citrophila* FERM-P 3150, *Kurthina zophii* ATCC 6900, *Mycoplana dimorpha* ATCC 4279, *Proteus rettgeri* FERM-P 8196, FERM-BP 941, AJ 2770, *Salmonella schottmuelleri* ATCC 8759, *Serratia marcescens* ATCC 14225, *Streptomyces humifer* FERM-P 2347, *Vibrio-tyrogenes* ATCC 7085, *Xanthomonas campestris* ATCC 7381, *Pichia membranaefaciens* IFO 0406, *Saccharomyces fermentati* IFO 0422, *Tremella brasiliensis* IFO 9289, *Alternaria cucumerina* IFO 7417, *Curvu-* laria geniculata ATCC 6671, *Fusarium nivale* ATCC 42308, *Helminthosporium gramineum* ATCC 6695, *Phoma destructiva* ATCC 24636, *Sclerotium bataticola* ATCC 12265, *Cochliobolus miyabeanus* IFO 5844, *Mucor circinelloides* ATCC 8770, *Aspergillus repens* ATCC 5817, *Penicillium decumbens* ATCC 10436, *Gromerella cingulata* ATCC 11326, *Septoria glycines* ATCC 38699, *Pseudoplea trifolii* IFO 7252, *Stemphylium astragali* IFO 7244, *Diplodia natalensis* ATCC alutaceum ATCC 18542, *Anixiella reticulata* ATCC 34511, *Arachniotus flavoluteus* ATCC 18430, *Byssochlamys fulva* ATCC 10099, *Coniochaeta tetraspora* ATCC 22275, *Golasinospora longispora* ATCC 18493, *Gymnoascus umbrinus* IFO 8358, *Microascus cinereus* ATCC 16594, *Microthecium retisporum* ATCC 22184, *Sordaria humana* ATCC 22796, *Sporormiella isomera* ATCC 24341, *Toxotrichum cancellatum* ATCC 15316 and *Melanospora zamiae* ATCC 12340; and isolating L-serine from said medium.

3. The process of claim 1 or 2, comprising carrying out the said reacting steps in an aqueous medium.

4. The process of claim 1 or 2, comprising running the said reacting steps at a temperature of from 15° to 60° C.

5. The process of claim 4, comprising using a temperature of from 30° to 40° C.

6. The process of claim 1 or 2, comprising using a pH of from 4 to 10.

7. The process of claim 1 or 2, comprising using a batch process or a continuous process.

* * * * *